United States Patent [19]

Scott

[11] Patent Number: 5,352,234
[45] Date of Patent: Oct. 4, 1994

[54] SURGICAL INSTRUMENT WITH ANGULAR SWIVEL

[75] Inventor: Tony D. Scott, Weatherford, Tex.

[73] Assignee: Midas Rex Pneumatic Tools, Inc., Fort Worth, Tex.

[21] Appl. No.: 958,229

[22] Filed: Oct. 8, 1992

[51] Int. Cl.$^5$ .................. A61B 17/32; A61B 17/00
[52] U.S. Cl. .................. 606/170; 285/184; 433/133; 433/130; 606/190
[58] Field of Search .................. 606/1, 170, 180, 190; 285/184, 118; 433/133, 130

[56] References Cited

U.S. PATENT DOCUMENTS

| | | | |
|---|---|---|---|
| 647,010 | 4/1900 | Marshall | 433/130 |
| 1,677,337 | 7/1928 | Grove . | |
| 2,557,507 | 6/1951 | Lang, Jr. | 285/184 |
| 2,886,262 | 5/1959 | Fletcher | 285/184 |
| 3,835,858 | 9/1974 | Hagen | 606/180 |
| 3,847,154 | 11/1974 | Nordin . | |
| 4,055,185 | 10/1977 | Waldron . | |
| 4,071,029 | 1/1978 | Richmond et al. . | |
| 4,281,989 | 8/1981 | Glover et al. | 433/130 |
| 4,738,476 | 4/1988 | Peaster | 285/184 |
| 4,747,406 | 5/1988 | Nash . | |
| 4,827,615 | 5/1989 | Graham | 30/166 |

Primary Examiner—Tamara L. Graysay
Attorney, Agent, or Firm—James E. Bradley; Mark D. Perdue

[57] ABSTRACT

A surgical instrument includes a conduit, the conduit having a conduit axis defined through a terminal end thereof, and a fluid-powered motor for rotating a dissecting tool, the motor having a longitudinal motor axis. A swivel member is connected in fluid communication between the motor and the conduit. The swivel member comprises a motor portion including a motor face inclined at a selected angle from the motor axis, and a conduit portion including a conduit face arranged oppositely that of the motor face and formed to engage matingly with the motor face. A connection shaft extends from one of the motor face and the conduit face and is engaged rotatably with a connection receptacle formed in another of the motor face and the conduit face. The swivel member is provided so that the motor is rotatable relative to the conduit from an aligned position, wherein the motor axis generally is aligned with the conduit axis, to an angularly displaced position, wherein the motor axis intersects the conduit axis at a selected angle.

12 Claims, 4 Drawing Sheets

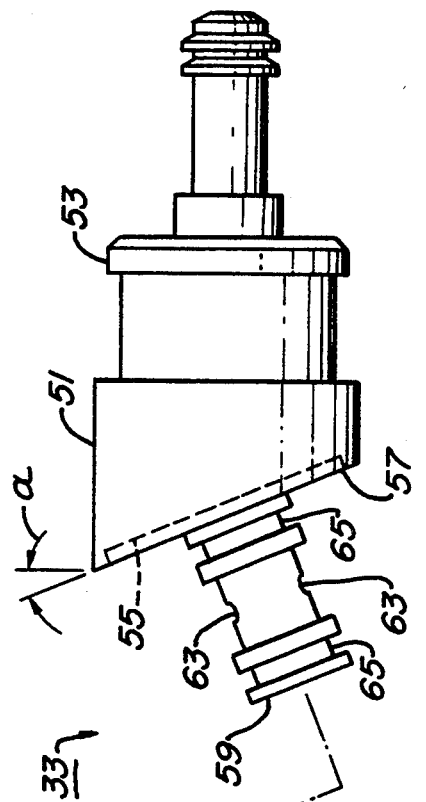
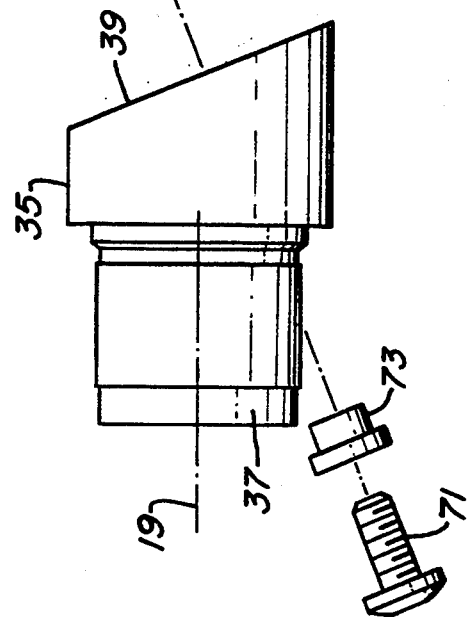
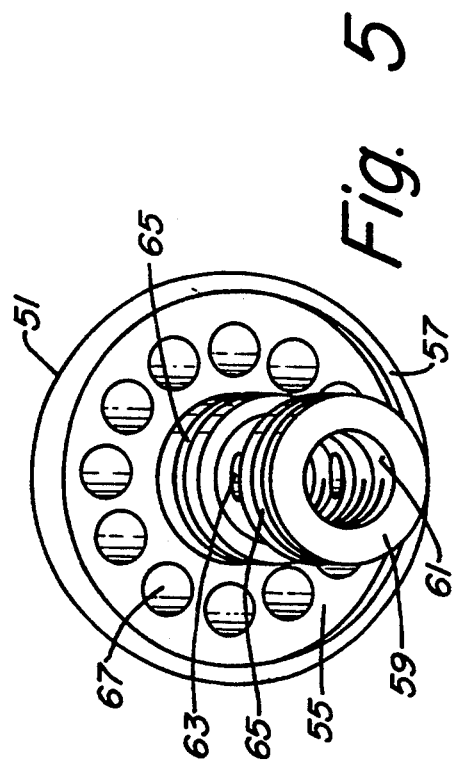
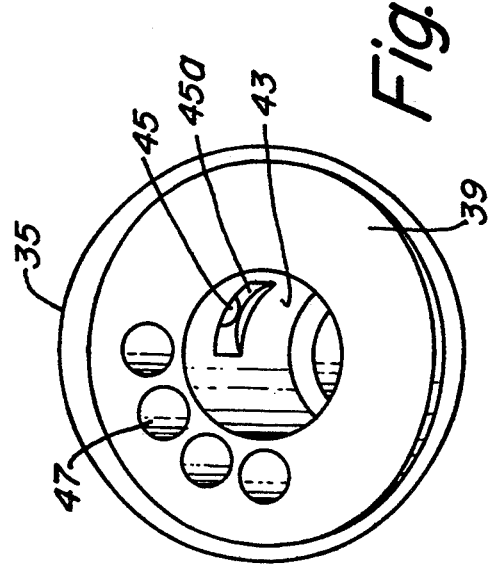

5,352,234

SURGICAL INSTRUMENT WITH ANGULAR SWIVEL

BACKGROUND OF THE INVENTION

1. Field of the Invention

The present invention generally relates to surgical instruments for the dissection of bone or other tissue. More particularly, the present invention relates to a swivel apparatus for attaching a surgical instrument motor to a fluid conduit, the apparatus providing the ability to swivel the motor into various angular displacements from the fluid conduit.

2. Background Information

Surgical instruments employing fluid-powered motors to rotate cutting or dissection tools are conventional and well-known in the art. Such surgical tools are used in such delicate surgical operations as brain surgery and microsurgery. These surgical instruments must be capable of sanitary operation without contaminating an operating-room environment. Also, because of the delicate nature of surgery, the surgical instrument must be manipulated easily by the surgeon without causing undue fatigue, which could lead to disastrous surgical errors.

A number of surgical tools have hand pieces or cutting ends that are angularly displaced with respect to the fluid conduit, which supplies the fluid pressure necessary to power the motor, which in turn rotates a cutting or dissecting tool. The angularly displaced hand piece and dissecting tool provides an advantageous arrangement for manipulation of the surgical tool by the surgeon or user. Such angled tools are disclosed, for example, in U.S. Pat. No. 1,677,337, Jul. 17, 1928 to Grove; U.S. Pat. No. 3,847,154, Nov. 12, 1974 to Nordin; U.S. Pat. No. 4,055,185, Oct. 25, 1977 to Waldron; U.S. Pat. No. 4,071,029, Jan. 31, 1978; and U.S. Pat. No. 4,827,615, May 9, 1989 to Graham.

A drawback of these angled surgical tools is that they are permanently angularly displaced from the fluid conduit. This is a drawback for the user because at some stages of the surgery, the user may desire a "straight" surgical tool, and at other times the user may desire an angled surgical tool. With the prior-art surgical tools, a surgeon either must have one of each type available, or must interchange straight and angled hand pieces with a single fluid conduit. Having each type of surgical tool available can be quite cumbersome because each surgical tool requires its own fluid conduit, which can be quite inconvenient during the pressure and stress of surgery. Switching between each type of surgical tool, on a single fluid conduit, can be time-consuming when time frequently is of the essence.

A need exists to provide a surgical instrument, including a fluid-powered motor for rotating a dissecting tool, that is manipulated easily from an aligned position in which the motor axis and the fluid conduit axis are aligned, to an angularly displaced position in which the motor axis intersects the fluid conduit axis at a selected angle.

SUMMARY OF THE INVENTION

It is a general object of the present invention to provide a surgical instrument for use in dissecting tissue that is capable of being manipulated from an aligned position to an angularly displaced position for improved manipulation of the surgical instrument by the user.

This and other objects are accomplished by providing a surgical instrument including a conduit, the conduit having a conduit axis defined through a terminal end thereof, and a fluid-powered motor for rotating a dissecting tool, the motor having a longitudinal motor axis. A swivel member is connected in fluid communication between the motor and the conduit. The swivel member comprises a motor portion including a motor face inclined at a selected angle from the motor axis, and a conduit portion including a conduit face arranged oppositely that of the motor face and formed to engage matingly with the motor face. A connection shaft extends from one of the motor face and the conduit face and is engaged rotatably with a connection receptacle formed in another of the motor face and the conduit face. The swivel member is provided so that the motor is rotatable relative to the conduit from an aligned position, wherein the motor axis generally is aligned with the conduit axis, to an angularly displaced position, wherein the motor axis intersects the conduit axis at a selected angle.

Other objects, features, and advantages of the present invention will be apparent to those skilled in the art with reference to the drawings and detailed description which follow.

DESCRIPTION OF THE DRAWINGS

FIG. 3 is an exploded elevation view of the swivel member of the surgical instrument of FIGS. 1 and 2.

FIG. 4 is an elevation end view of the conduit portion of the swivel member illustrated in FIG. 3.

FIG. 5 is an elevation view of the motor portion of the swivel member illustrated in FIG. 3.

DESCRIPTION OF THE PREFERRED EMBODIMENT

Figure 1:
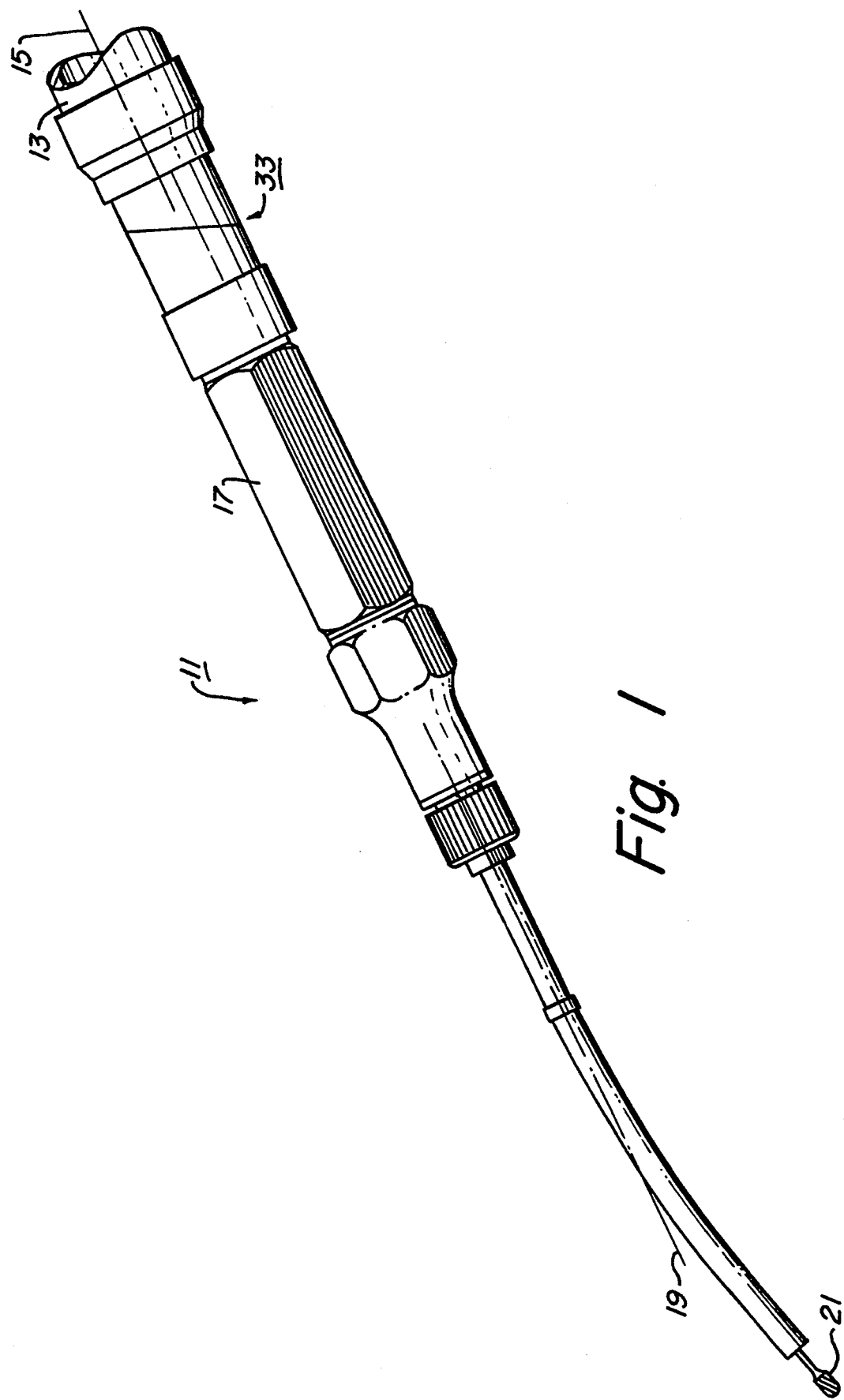
FIG. 1 is an elevation view of a surgical instrument according to the present invention shown in an aligned position.

Referring now to the Figures, and particularly to FIG. 1, the surgical instrument according to the present invention will be described. FIG. 1 illustrates, in elevation view, a surgical instrument 11 according to the present invention. Surgical instrument 11 comprises a fluid conduit 13 having a longitudinal conduit axis 15 defined at a terminal end thereof. Fluid conduit 13 is connected in fluid communication with a fluid-powered motor 17, which has a longitudinal motor axis 19. Motor 17 rotates a cutting or dissecting tool 21 in response to fluid pressure from fluid conduit 13. A swivel means or member 33 is connected in fluid communication between fluid conduit 13 and motor 17. FIG. 1 depicts surgical instrument 11 in an aligned position in which longitudinal conduit axis 15 and longitudinal motor axis 19 are substantially aligned.

Figure 2:
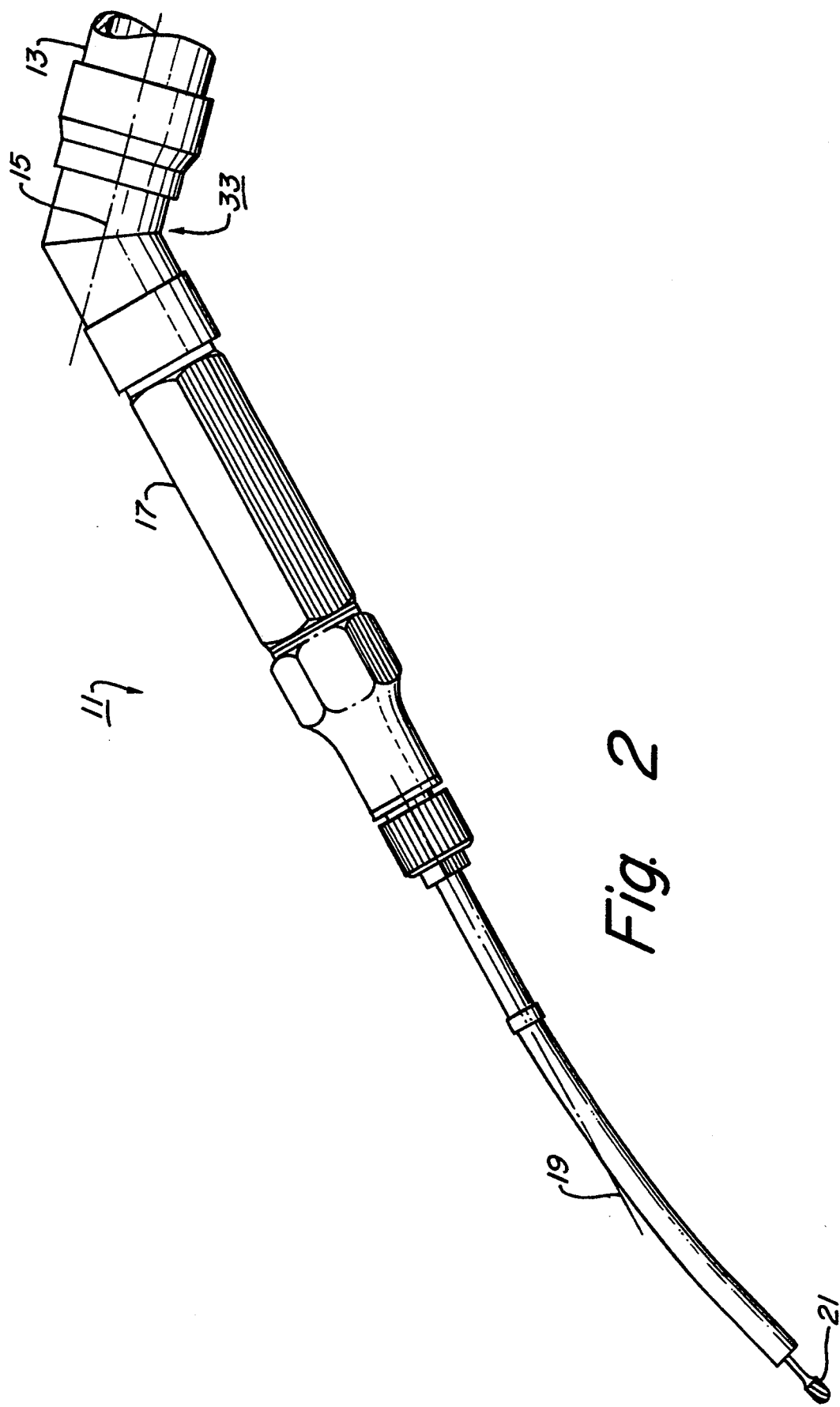
FIG. 2 is an elevation view of the surgical instrument according to the present invention shown in an angularly displaced position.

FIG. 2 depicts surgical instrument 11 of FIG. 1 in an angularly displaced position in which longitudinal conduit axis 15 and longitudinal motor axis 19 intersect at a selected angle. Preferably, the selected angle between longitudinal conduit axis 15 and longitudinal motor axis 19 is 45 degrees, measured as the acute angle included between axes 15, 19. Swivel means or member 33 permits manipulation of surgical tool 11 from the aligned position, illustrated in FIG. 1, to the angularly displaced position illustrated in FIG. 2.

Referring now to FIGS. 3 through 6, swivel member 33 comprises a motor portion 35 for connection in fluid communication to the motor (17 in FIGS. 1 and 2) at one end 37 thereof. An inclined motor face 39 is provided at an opposite end of motor portion 35. Inclined motor face 39 is inclined at a selected angle $\alpha$, which is measured normally to longitudinal motor axis 19. Preferably, angle $\alpha$ is 22.5 degrees, which yields an ultimate angular displacement of 45 degrees.

A motor portion 35 is further provided with a connection receptacle 43 formed in motor face 39. Connection receptacle 43 is cylindrical and is normal to motor face 39. A motor fluid inlet passage 45 is formed in connection receptacle 43 for fluid communication with pair of fluid ports 63. Inlet passage 45 delivers air pressure to rotate motor 17. Inlet passage 45 terminates in semi-annular recess 45a in receptacle 43. Motor portion 35 is further provided with a plurality, in this case four, of motor fluid exhaust passages 47. Exhaust passage 47 provides a return for the air delivered to motor 17.

Figure 6:
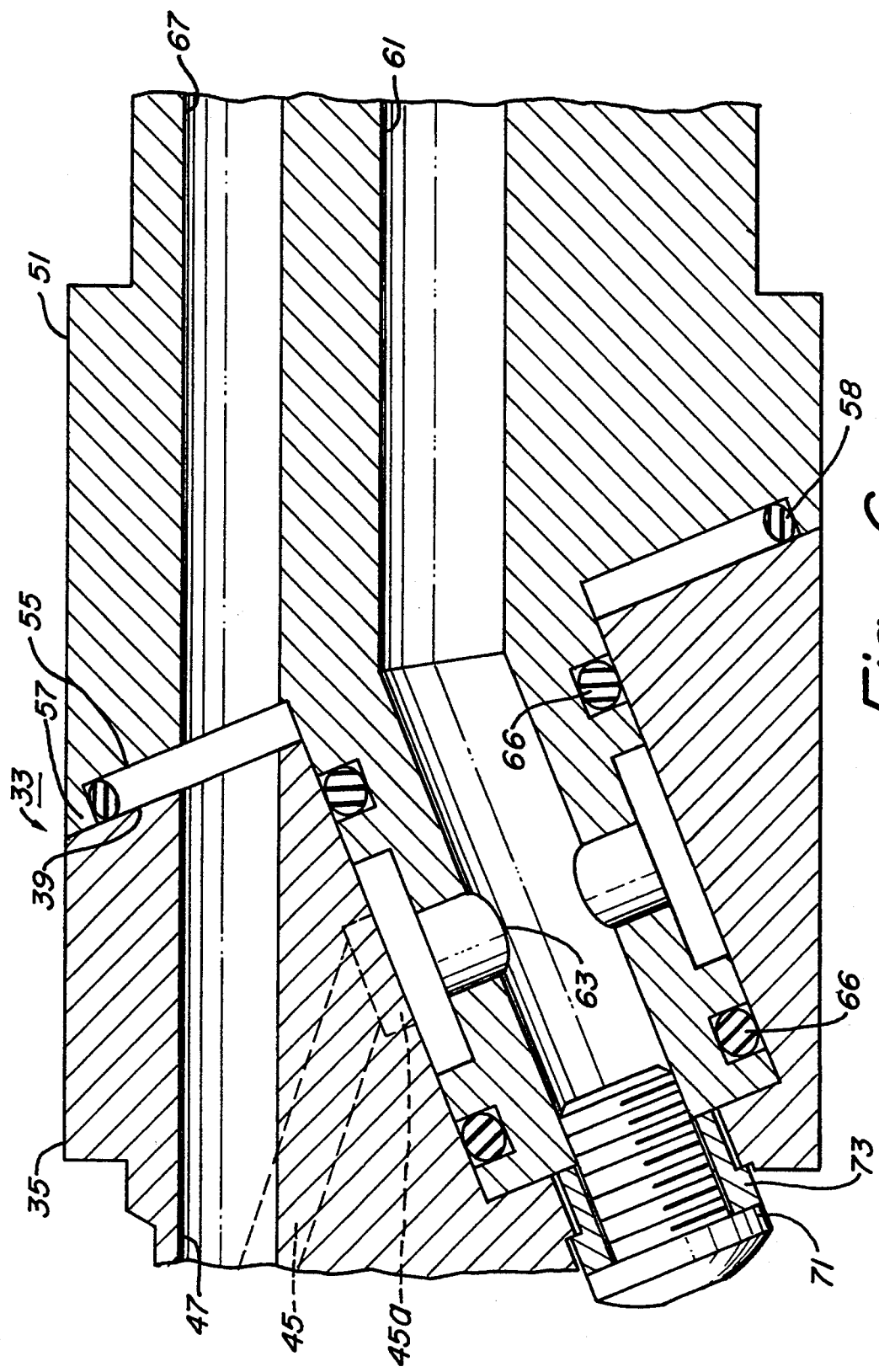
FIG. 6 is a fragmentary, longitudinal section view of the assembled swivel member, illustrating the engagement of the various parts thereof.

Swivel member 33 also comprises a conduit portion 51 for connection in fluid communication at one end 53 thereof with fluid conduit (12 in FIGS. 1 and 2). Conduit portion 51 is further provided with a conduit face 55, which is arranged oppositely motor face 39, and is adapted to engage matingly with motor face 39. Conduit face 55 is further provided with conduit face lip 57, which cooperates with motor face 39 to define a receptacle for a sealing member 58 (FIG. 6).

A hollow, internally threaded connection shaft 59 extends from and normally to conduit face 55. Connection shaft 59 is adapted for mating engagement with connection receptacle 43 (FIG. 6) in motor portion 35. Connection shaft 59 is provided with a pair of fluid ports 63 extending through its sidewall for communication with fluid inlet recess 45a and passage 45 in motor portion 35. Connection shaft 59 is further provided with a pair of seal receptacles 65 for receiving seal members 66 for sealing engagement of connection shaft 59 with connection receptacle 43 of motor portion 35.

A conduit fluid inlet passage 61 (FIG. 6) is formed centrally through and coaxially with connection shaft 59 and conduit portion 51. A plurality of conduit fluid exhaust passages 67 are formed in conduit portion 51 and are circumferentially spaced about connection shaft 59, as illustrated in FIG. 5.

A fastening means 71, in this case a screw, is provided to secure connection shaft 59 of conduit portion 51 in the connection receptacle of motor portion 35, wherein motor face 39 and conduit face lip 57 are engaged rotatably and matingly. Fastener 71 is further provided with an anti-friction bushing 73 to insure smooth and free rotation of motor portion 35 relative to conduit portion 51.

FIG. 6 depicts, in partial longitudinal section, assembled swivel member 33 and the mating rotatable engagement between motor portion 35 and conduit portion 51. As illustrated, connection shaft 59 of motor portion 51 is received by connection receptacle 43 of motor portion 35. Fluid inlet communication is established between fluid conduit 13 and motor 17 through conduit fluid inlet passage 61 in conduit portion 51, fluid ports 63, connection shaft 59, and motor fluid inlet passage 45. Connection shaft 59 is sealed against fluid leakage within connection receptacle 43 by seal members 66, in this case O-rings, fit in seal receptacles 65 of connection shaft 59.

Fluid exhaust communication is established between motor 17 (FIG. 1) and fluid conduit 13 (FIG. 1) by motor fluid exhaust passages 47, which mate with conduit fluid exhaust passages 67 at the interface between motor inclined face 39 and mating conduit face 55. Motor face 39 and conduit face lip 57 cooperate to define a seal receptacle for receiving face seal member 58, in this case, an O-ring, for sealing motor face 39 and conduit mating face 55 against fluid leakage therebetween.

As is illustrated, not all of the plurality of conduit fluid exhaust passages 67 will align with mating motor fluid exhaust passages 47. However, a sufficient number of motor fluid exhaust passages 47 will align with conduit fluid exhaust passages 67 to permit exhaust of fluid from motor 17 (FIG. 1), if swivel member 33 is constructed as illustrated in FIGS. 4 and 5. Rotating conduit portion 51 relative to motor portion 35 causes different alignment of exhaust passage 47 with exhaust passages 67.

With reference to FIG. 1 through 6, the operation of surgical instrument 11 according to the present invention will be described. Surgical instrument 11, including fluid conduit 13, motor 17, dissection tool 21, and swivel member 33 is assembled and connected in fluid communication with a fluid pressure source (not shown), which is typically a operating room's compressed air supply.

Surgical operations, typically dissection of bone or other tissue, then are commenced using surgical instrument 11. The user or surgeon may desire that surgical instrument 11 be configured initially in the aligned position, in which motor longitudinal axis 19 is aligned with and substantially coaxial with longitudinal fluid conduit axis 15. Fluid pressure then is supplied from the fluid pressure source (not shown), through fluid inlet passage 61, fluid ports 63, and motor fluid inlet passage 45 to motor 17, which rotates dissection tool 21 for dissection of tissue. Fluid pressure is exhausted through motor exhaust passages 47, which mate at the interface of inclined motor face 39 and mating conduit face 55 with at least a portion of conduit exhaust passages 67.

After the initial dissection operation is accomplished, the user or surgeon may desire to rotate motor 17 relative to fluid conduit 13 so that surgical instrument 11 is in an angularly displaced position, in which motor axis 19 intersects conduit axis 15 at a selected angle. The angularly displaced position of surgical instrument 11 is desirable to permit more careful and minute manipulation of dissection tool 27 after the initial dissection is accomplished.

The angularly displaced position is achieved by rotating motor 17 and motor portion 35 of swivel 33 about connection shaft 59 of conduit portion 51. Motor inclined face 39 and oppositely facing conduit face lip 57 cooperate to angularly displace motor 17 relative to fluid conduit 13. Seal members 58, 66 maintain sealing engagement between faces 39, 55 and connection shaft 59 and connection receptacle 43 during rotation of motor 17 relative to fluid conduit 13.

In the angularly displaced position, pressurized fluid is delivered from fluid pressure source (not shown) to motor 17 through conduit fluid inlet passage 61, fluid port 63, and motor fluid inlet passage 45. Motor 17 rotates dissecting tool 21 for dissection operation. Fluid pressure is exhausted from motor 17 through motor fluid exhaust passages 47, which mate, at the interface of inclined motor face 41 and mating conduit face 55, with at least a portion of conduit exhaust passages 67. Despite the rotation of motor portion 35 of swivel member 33 with respect to conduit portion 51 of swivel member 33, motor fluid exhaust passages 47 register with and remain aligned with a portion of conduit fluid passages 67, to permit free exhaust of fluid pressure from motor 17. Therefore, fluid inlet and exhaust communication between motor 17 and fluid conduit 13 exists at all times, regardless of the angular displacement of the motor 17 from conduit 13.

In subsequent operations, motor 17 may be rotated relative to conduit 13 from the aligned position to the angularly displaced position, and vice-versa, any number of times.

The surgical instrument according to the present invention has a number of advantages. A principal advantage of the present invention is that the motor may be rotated with respect to the fluid conduit from an aligned position to an angularly displaced position. This advantage obviates the necessity of interchanging straight and angled surgical instruments on a single fluid conduit. This advantage also obviates the need to have straight and angled surgical instruments connected to individual fluid conduits.

Provision of a surgical instrument with the ability to swivel from an aligned position to an angularly displaced position permits the user of the instrument to switch quickly and easily to an instrument configuration that is most appropriate for the operation being undertaken. Such flexibility of configuration eliminates fatigue and speeds surgical operations.

The present invention has been described with reference to a preferred embodiment thereof. Those skilled in the art will recognize that the present invention is susceptible to variations and modifications without departing from the scope thereof.

I claim:

1. In a surgical instrument for dissecting tissue, the surgical instrument including a conduit having a conduit axis defined through a terminal end thereof, and a fluid powered motor for rotating a dissecting tool, the motor having a longitudinal motor axis, the improvement comprising:
   connection means for rotatably connecting the motor to the conduit; and
   the connection means including swivel means for swiveling the motor relative to the conduit from an aligned position, wherein the motor axis is aligned with the conduit axis, to an angularly displaced position, wherein the motor axis intersects the conduit axis at a selected included angle, the swivel means comprising:
      a motor portion in fluid communication with the motor;
      a conduit portion in fluid communication with the conduit;
      a connection shaft extending from one of the portions;
      a connection receptacle formed in the other of the portions, the connection receptacle formed to receive the connection shaft in rotatable engagement; and
      fastener means for securing the connection shaft in rotatable engagement with the connection receptacle.

2. The surgical instrument according to claim 1, wherein the connection means further comprises:
   a motor inclined face on the motor portion; and
   an oppositely facing conduit inclined face on the conduit portion formed to sealingly engage the motor inclined face.

3. The surgical instrument according to claim 1 further comprising means for sealing the connection means against fluid leakage therefrom.

4. The surgical instrument according to claim 1 further comprising:
   inlet passage means extending through the connection means for delivering pressurized fluid to the motor; and
   exhaust passage means extending through the connection means for exhausting pressurized fluid from the motor.

5. A surgical instrument for dissecting tissue, the surgical instrument comprising:
   a motor responsive to fluid pressure to rotate a dissecting tool having a cutting head, the motor including a longitudinal motor axis;
   a conduit connected in fluid communication to the motor to provide fluid pressure to the motor from a fluid pressure source, the conduit including a longitudinal conduit axis defined at a terminal end thereof; and
   a swivel to permit the motor to swivel from an aligned position, wherein the motor axis is substantially aligned with the conduit axis, to an angularly displaced position, wherein the motor axis intersects the conduit axis at a selected angle, the swivel including:
      a motor portion connected in fluid communication with the motor, the motor portion including a motor face inclined at a selected angle from the motor axis;
      the conduit portion connected in fluid communication with the conduit, the conduit portion having a conduit face arranged oppositely that of the motor face, the conduit face formed to matingly engage with the motor face;
      a connection receptacle formed in one of the faces;
      a connection shaft extending from the other of the faces, into rotatable engagement with a connection receptacle;
      a first inlet flow passage formed in one of the portions extending into the connection shaft;
      a second inlet flow passage formed in the other portion and terminating in the connection receptacle so that fluid will flow through the first to the second inlet flow passage to supply fluid pressure to the motor regardless of the angular position of the conduit portion relative to the motor portion;
      a plurality of motor exhaust passages formed in the motor portion and terminating at the motor face;
      a plurality of mating conduit exhaust passages formed in the conduit portion and terminating at the conduit face, so that wherein at least one mating conduit exhaust passage mates in fluid communication with at least one of the motor exhaust passages;
      a face seal member sealingly engaged between the motor face and the mating conduit face and surrounding the ends of the exhaust flow passage; and at least one connection seal member engaged between the connection shaft and the connection receptacle.

6. In a surgical instrument for dissecting tissue, the surgical instrument including a conduit having a conduit axis defined through a terminal end thereof, and a fluid-powered motor for rotating a dissecting tool, the motor having a longitudinal motor axis, the improvement comprising:
- a motor portion connected in fluid communication with the motor, the motor portion including a motor face inclined at a selected angle from the motor axis;
- a conduit portion connected in fluid communication with the conduit, the conduit portion having a conduit face arranged oppositely that of the motor face, the conduit face formed to rotatably engage with the motor face;
- a connection receptacle formed in one of the faces;
- a connection shaft extending from the other of the faces into rotatable engagement with the connection receptacle; and
- wherein the motor and motor portion are rotatable relative to the conduit and conduit portion from an aligned position, wherein the motor axis generally is aligned with the conduit axis, to an angularly displaced position, wherein the motor axis intersects the conduit axis at a selected angle.

7. The surgical instrument according to claim 6 further comprising:
- a motor inlet flow passage formed in the motor portion;
- a mating conduit inlet flow passage formed in the conduit portion; and
- communication means for communicating the motor inlet flow passage with the conduit inlet flow passage regardless of the angular position of the conduit portion relative to the motor portion.

8. The surgical instrument according to claim 6 further comprising:
- a plurality of motor exhaust flow passages formed in the motor portion, each having an end terminating at the motor face;
- a plurality of mating conduit exhaust flow passages formed in the conduit portion, each having an end terminating at the conduit face, wherein at least one of the motor exhaust flow passages communicates with at least one conduit exhaust flow passages regardless of the angular position of the conduit portion relative to the motor portion; and
- seal means for sealing the conduit and motor portins to each other against fluid leakage.

9. The surgical instrument according to claim 6 further comprising a face seal member disposed between the motor face and the conduit face.

10. The surgical instrument according to claim 6 further comprising at least one connection seal member disposed between the connection shaft and the connection receptacle.

11. The surgical instrument according to claim 6, wherein the motor face is inclined at an angle of substantially 22.5 degrees, and the selected angle of the angularly displaced position is substantially 45 degrees.

12. The surgical instrument according to claim 6 further comprising:
- a motor inlet flow passage formed in the motor portion, through the connection shaft and terminating therein; and
- a conduit inlet flow passage formed in the conduit portion and terminating therein, wherein inlet fluid communication is established between the motor and the fluid conduit.

* * * * *